United States Patent
Leschinsky

(10) Patent No.: US 8,974,491 B2
(45) Date of Patent: Mar. 10, 2015

(54) METHODS FOR ADAPTIVE LIMB OCCLUSION

(71) Applicant: Infarct Reduction Technologies Inc., Waldwick, NJ (US)

(72) Inventor: Boris Leschinsky, Mahwah, NJ (US)

(73) Assignee: Infarct Reduction Technologies Inc., Waldwick, NJ (US)

( * ) Notice: Subject to any disclaimer, the term of this patent is extended or adjusted under 35 U.S.C. 154(b) by 34 days.

(21) Appl. No.: 13/836,418

(22) Filed: Mar. 15, 2013

(65) Prior Publication Data

US 2013/0211269 A1    Aug. 15, 2013

Related U.S. Application Data

(63) Continuation-in-part of application No. 13/351,257, filed on Jan. 17, 2012, now Pat. No. 8,795,323, and a continuation-in-part of application No. 13/362,039, filed on Jan. 31, 2012, now Pat. No. 8,753,283, which (Continued)

(51) Int. Cl.
*A61B 17/00* (2006.01)
*A61B 17/135* (2006.01)
(Continued)

(52) U.S. Cl.
CPC .......... *A61B 17/1355* (2013.01); *A61B 5/02233* (2013.01); *A61B 5/0002* (2013.01); *A61B 5/02225* (2013.01); *A61B 5/0225* (2013.01); *A61B 5/1112* (2013.01)
USPC ....................................................... 606/202

(58) Field of Classification Search
CPC ............. A61B 17/1355; A61B 17/132; A61B 17/135; A61B 5/02; A61B 5/02225; A61B 5/02233; A61B 5/0225

USPC .......... 606/202, 203; 600/485, 490, 491, 495, 600/496, 499
See application file for complete search history.

(56) References Cited

U.S. PATENT DOCUMENTS 4,479,494 A * 10/1984 McEwen ....................... 606/202
5,687,732 A    11/1997 Inagaki
(Continued)

FOREIGN PATENT DOCUMENTS

| WO | WO/2012/016280 | 2/2012 |
| WO | WO/2012/090068 | 7/2012 |
| WO | WO/2012/142360 | 10/2012 |

OTHER PUBLICATIONS

Tarakada Y et al. Applications of vascular occlusion diminish disuse atrophy of knee extensor muscles. Medicine & Science in Sports & Exercise, vol. 32, No. 12, 2000, pp. 2035-2039.

(Continued)

*Primary Examiner* — Alexander Orkin
(74) *Attorney, Agent, or Firm* — Boris Leschinsky

(57) ABSTRACT

Methods for adaptive cuff inflation for the purposes of occluding a limb of a subject include inflating a cuff to a pressure at or above limb occlusion pressure and periodically deflating the cuff to detect amplitude of oscillometric oscillations reaching or exceeding a predetermined threshold, whereby indicating that the cuff pressure has reached an updated systolic blood pressure. Selecting the cuff to be wide enough to define limb occlusion pressure at or below the systolic blood pressure assures that this maneuver does not compromise cessation of blood flow to the limb. Devices are disclosed configured to operate in at least two of the following three operating modes: a tourniquet mode, a remote conditioning mode and a blood pressure monitoring mode.

11 Claims, 5 Drawing Sheets

Related U.S. Application Data is a continuation of application No. 12/820,273, filed on Jun. 22, 2010, now Pat. No. 8,114,026.

(60) Provisional application No. 61/219,536, filed on Jun. 23, 2009, provisional application No. 61/256,038, filed on Oct. 29, 2009.

(51) Int. Cl.
*A61B 5/022* (2006.01)
*A61B 5/0225* (2006.01)
*A61B 5/00* (2006.01)
*A61B 5/11* (2006.01)

(56) References Cited

U.S. PATENT DOCUMENTS

| | | | | |
|---|---|---|---|---|
| 5,836,887 | A * | 11/1998 | Oka et al. | 600/494 |
| 6,152,881 | A | 11/2000 | Raines | |
| 7,657,135 | B2 * | 2/2010 | Borgos et al. | 385/12 |
| 7,885,710 | B2 | 2/2011 | Sih | |
| 8,246,548 | B2 | 8/2012 | Naghavi | |
| 2008/0262533 | A1 * | 10/2008 | McEwen et al. | 606/202 |
| 2010/0105993 | A1 | 4/2010 | Naghavi | |
| 2010/0160799 | A1 | 6/2010 | Caldarone | |
| 2010/0185220 | A1 | 7/2010 | Naghavi | |
| 2010/0292619 | A1 | 11/2010 | Redington | |
| 2010/0305607 | A1 | 12/2010 | Caldarone | |
| 2011/0190807 | A1 | 8/2011 | Redington | |
| 2011/0224606 | A1 | 9/2011 | Shome | |
| 2011/0238107 | A1 | 9/2011 | Raheman | |
| 2011/0240043 | A1 | 10/2011 | Redington | |
| 2011/0251635 | A1 | 10/2011 | Caldarone | |
| 2012/0277789 | A1 | 11/2012 | Caldarone | |

OTHER PUBLICATIONS

Deloughry JL and Griffiths R. Arterial Tourniquets. Continuing Education in Anaesthesia, Critical Care and Pain 9;2:56-60, 2009.

Murphy CG, Winter DC, Bouchier-Hayes DJ. Tourniquet injuries: pathogenesis and modalities of attenuation. Acta Orthop Belg. 71:635-645, 2005.

Rowse A. The pathophysiology of an arterial tourniquet: a review. Southern African Journal of Anaesthesia and Analgesia, pp. 22-29, Nov. 2002.

Kragh JF, Swan KG, Smith DC, Mabry RL, Blackbourne LH. Historical review of emergency tourniquet use to stop bleeding. The American Journal of Surgery 203;2:242-252.

* cited by examiner

METHODS FOR ADAPTIVE LIMB OCCLUSION

CROSS-REFERENCE DATA

This application is a continuation-in-part of my U.S. patent application Ser. No. 13/351,257, now U.S. Pat. No. 8,795,323, filed Jan. 17, 2012 and entitled "Dual-Mode Remote Ischemic Preconditioning Devices and Methods". This application is also a continuation-in-part of my U.S. patent application Ser. No. 13/362,039, now U.S. Pat. No. 8,753,283, entitled "AUTOMATIC DEVICES FOR REMOTE ISCHEMIC PRECONDITIONING" filed 31 Jan. 2012, which is in turn a continuation of the U.S. patent application Ser. No. 12/820,273, now U.S. Pat. No. 8,114,026, entitled "METHODS AND DEVICES FOR REMOTE ISCHEMIC PRECONDITIONING AND NEAR-CONTINUOUS BLOOD PRESSURE MONITORING" filed Jun. 22, 2010, now U.S. Pat. No. 8,114,026 which in turn claims a priority benefit from the U.S. Provisional Patent Application No. 61/219,536 filed Jun. 23, 2009 entitled "BLOOD PRESSURE CUFF INCORPORATING A PRECONDITIONING DEVICE" and the U.S. Provisional Patent Application No. 61/256,038 filed Oct. 29, 2009 entitled "PRECONDITIONING DEVICES FOR USE IN AMI AND PERCUTANEOUS INTERVENTION SETTINGS", all cited documents incorporated herein by reference in their entirety.

BACKGROUND OF THE INVENTION

The present invention relates generally to limb occlusion devices. In particular, the present invention describes a limb occlusion device capable of performing more than one function, for example as a limb occlusion tourniquet, as a blood pressure monitor and as a device for automatic delivery of remote conditioning treatment.

Inflatable limb occlusion devices generally include a cuff sized to be placed about a limb such as an upper arm or a thigh of a subject and a controller operably connected to or incorporated with the cuff and configured for inflating and deflating the cuff to achieve a desired function. One example of such function may be to detect the subject's blood pressure by slowly inflating or deflating the cuff while recording oscillometric oscillations (also known as an oscillometric envelope) from which systolic, diastolic and mean arterial blood pressure of the subject may be determined—see FIG. 2. Another example of such desired function is to provide a more prolonged limb occlusion for the purpose of causing cessation of blood flow to the limb—for example during a knee surgery to provide a bloodless field or as an emergency tourniquet designed to stop blood loss through the bleeding extremity. Yet another example of such desired function may be to deliver a therapy called remote conditioning.

The term "remote conditioning" is used in this disclosure to describe a recently discovered therapy in which one or more limbs are subjected to a series of intermittent occlusions of blood flow followed by restorations of blood flow. The terms "limb occlusion" and "cessation" of blood flow are used in this disclosure to describe a reduction of 90% or more of the blood flow through the limb as compared with unrestricted blood flow. In a typical scenario, 5-min occlusion of blood flow to a certain limb such as an upper arm or a thigh is followed by 5-min release. This treatment cycle may be repeated 4 times making the entire procedure to last about 40 minutes. The duration or each occlusion and each release and the number of treatment cycles may vary: each occlusion and each release may last respectively from about 1 minute to about 20 min, and the number of treatment cycles may be from 2 to 20. The therapy of "remote conditioning" is sometimes referred to in the literature as "ischemic conditioning", "remote ischemic conditioning", "remote ischemic peri-conditioning", "remote ischemic preconditioning", "remote ischemic perconditioning", or "remote ischemic postconditioning", depending on whether this procedure is applied before or after either the initial occlusion event (such as for example an acute myocardial infarction or stroke) or a treatment of such event involving restoration of blood flow to the target organ. In any case, all of these modalities are generally referred to as remote conditioning in this description.

The therapy of remote conditioning has been demonstrated to be clinically beneficial in a variety of circumstances using a manually-operated blood pressure cuff. Many of such circumstances involve a clinical situation in which perfusion (normal blood flow to a target organ or tissue) is temporarily interrupted leading to ischemia (lack of oxygen delivery to the organ). This may occur either deliberately—during surgery for example—or as a result of a disease, for example a heart attack or stroke. Restoration of perfusion is known to trigger a so-called ischemia-reperfusion injury, which further exacerbates the original ischemic injury and increases infarct size—by as much as 50%. Prevention or at least attenuation of ischemia-reperfusion injury has valuable clinical benefits and remote conditioning is shown to be the most potent known method providing this benefit.

Remarkably, in over 100 published clinical trials of remote conditioning on over 10,000 patients worldwide, there are no reported side effects or complications associated with this non-invasive procedure making it especially attractive and safe to use.

Despite the fact that all three modalities described above (limb tourniquet, blood pressure monitor, and device for remote conditioning) may be accomplished by using an inflatable cuff, there are no known devices configured to accomplish more than one of these modalities. Well known are stand-alone blood pressure monitors, stand-alone limb occlusion tourniquets, and stand-alone remote conditioning devices. Yet, in many clinical circumstances, the subject may benefit if more than one modality is delivered on the same limb and by the same device. There is a need therefore for a multi-mode inflatable limb occlusion device that may provide any two or all three operating modes described above.

SUMMARY OF THE INVENTION

Accordingly, it is an object of the present invention to overcome these and other drawbacks of the prior art by providing novel methods of adaptive limb occlusion allowing automatic determination of minimal cuff occlusion pressure and periodic adjustment thereof to follow changes in blood pressure of the subject.

It is another object of the invention to provide a novel inflatable limb occlusion device that can be operated in any two or all three of the following operating modes: limb tourniquet, blood pressure monitor, and remote conditioning device.

It is yet a further object of the present invention to provide a self-contained multi-mode limb occlusion device which can operate as a smart tourniquet once activated; the cuff in this tourniquet is inflated to the minimal occlusion pressure to stop the bleeding through the limb. Such optimal cuff pressure may be automatically determined by the device and adjusted depending on the changes in the blood pressure of the subject.

It is a further object of the present invention to provide a multi-mode inflatable limb occlusion device configured to be self-contained and incorporated within or on the cuff such that no wires or tubes are extending from such device to an external controller.

It is yet a further object of the present invention to provide a multi-mode inflatable limb occlusion device incorporated with a hospital-grade patient monitor or a home-based blood pressure monitor, in which a cuff is pneumatically driven and attached to a controller with a piece of tube.

It is yet another object of the present invention to provide a multi-mode device configured for operating during orthopedic surgery by first delivering remote conditioning to the subject and then providing a tourniquet function for the duration of surgery.

The multi-mode inflatable limb occlusion device of the invention includes generally a cuff and a controller. The cuff may be sized to be tightly wrapped about the limb of the subject such as an upper arm or a thigh. In embodiments, the width and length of the cuff may be selected to be the same as a standard blood pressure cuff. In other embodiments, the cuff width may be greater than the standard cuff width. In yet other embodiments, the cuff may include one bladder, while in other embodiments, it may include two bladders, one being proximal to the other along the limb of the subject. The one or two bladders may be incorporated into the cuff itself using design concepts termed "bladderless cuff" in which instead of a physical bladder contained inside the layers of cuff fabric, the bladder is formed by sealing two layers of the cuff together, whereby reducing the thickness of the cuff.

The controller may include a power supply, such as a rechargeable or disposable battery, or a continuous power supply using AC line. The controller may also include at least one pressure sensor configured for monitoring internal cuff pressure, an air pump to inflate the cuff, a number of valves configured for cuff inflation and controlled deflation, a central processor, which may include a main and a secondary CPU, an optional display and user interface including a START button and optional mode selection or other buttons. The details of these arrangements are described in my previously filed patent applications cited above.

Disclosed are methods for adaptive limb occlusion of a subject, one of these methods comprising the steps of:
  (a) determining systolic blood pressure of a subject, for example by inflating a cuff placed about a limb of the subject;
  (b) calculating a limb occlusion pressure using the systolic blood pressure determined in step (a);
  (c) inflating the cuff to a pressure at or above the limb occlusion pressure calculated in step (b) for a period of cuff inflation to cause cessation of blood flow through the limb, the period of cuff inflation lasting at least one minute;
  (d) at least once during the period of cuff inflation, reducing cuff pressure sufficiently to determine updated systolic blood pressure of the subject;
  (e) calculating updated limb occlusion pressure using the updated systolic blood pressure determined in step (d); and
  (f) inflating the cuff to a pressure at or above the updated limb occlusion pressure calculated in step (e).

Step (d) of the method may further include reducing cuff pressure until the amplitude of detected oscillometric oscillations reaches or exceeds a predetermined threshold—over one or several consecutive heart beats.

Steps (d) through (f) may be repeated on a scheduled basis throughout the period of cuff inflation whereby the cuff pressure may be made to track fluctuating blood pressure of the subject.

Steps (c) and (f) may further be conducted by inflating the cuff to a pressure exceeding the limb occlusion pressure by a predetermined safety margin, for example 1 mmHg; 5 mmHg; 10 mmHg; 15 mmHg; 20 mmHg; 30 mmHg; 50 mmHg; 70 mmHg or any value in-between.

Keeping the predetermined safety margin low and frequently detecting updated systolic blood pressure of the subject allows occluding the limb at the lowest cuff pressure, whereby minimizing tissue compression, pain, risk of nerve compression and other complications following removal of the cuff.

According to some embodiments of the invention, limb occlusion of the subject may be conducted once for an extended period of time of up to 3 hours, such as in a tourniquet mode. In other embodiments, a plurality of shorter limb occlusions alternating with periods of limb reperfusion (when the blood flow is at least partially restored) may be applied—such as when delivering remote conditioning therapy.

In embodiments, there is disclosed another method for adaptive limb occlusion of a subject, the method comprises the steps of:
  (a) providing a cuff placed about the limb, the cuff configured to define a limb occlusion pressure to be equal to or below a systolic blood pressure of the subject;
  (b) inflating the cuff to a pressure at or above the limb occlusion pressure of the subject for a period of cuff inflation lasting at least one minute;
  (c) continuously or intermittently monitoring cuff pressure for an indication that the cuff pressure is at or below systolic blood pressure of the subject; and
  (d) when the cuff pressure is at or below the systolic blood pressure of the subject and the cuff pressure is at or above the limb occlusion pressure of the subject, inflate the cuff to a pressure exceeding the limb occlusion pressure by a predetermined safety margin,
  whereby maintaining cessation of blood flow to the limb throughout the period of cuff inflation.

Step (a) of the method may include providing a cuff with a ratio of cuff width to cuff circumference as 1:3 or greater.

Step (b) may include an additional step of inflating the cuff to a pressure sufficiently high as to determine the subject's systolic blood pressure and then an additional optional step of calculating limb occlusion pressure using cuff dimensions and systolic blood pressure information as described in my cited previous patent applications.

Step (b) may further include inflating the cuff to a pressure exceeding the limb occlusion pressure by a predetermined safety margin and then deflating the cuff at least once or on a scheduled basis until new systolic pressure is detected in step (c).

Step (c) may further include monitoring of the amplitude of oscillometric oscillations as an indicator of cuff pressure reaching systolic blood pressure level—which occurs when the amplitude of oscillometric oscillations increases from a noise level and reaches a predetermined threshold.

The method may further include steps to minimize cuff pressure needed for maintaining of limb occlusion—by selecting more frequent checks of systolic blood pressure in step (b) and by lowering the safety margin in step (d).

The controller may be configured to operate in at least two of the following three operating modes:
  (a) a remote conditioning mode, in which the controller may be configured to inflate and deflate the cuff according to a remote conditioning treatment protocol including two or more treatment cycles, each treatment cycle including:
  i. a period of cuff inflation, during which the cuff may be inflated and maintained at a pressure at or above the limb occlusion pressure of the subject for at least about one minute, and
  ii. a period of cuff deflation, during which the cuff may be deflated so as to least partially restore blood flow through the limb,
(b) a tourniquet mode, in which the controller may be configured to inflate the cuff to at least the limb occlusion pressure for a predetermined or manually set period of cuff inflation lasting at least one minute, and
(c) a blood pressure monitoring mode, in which the controller may be configured to detect blood pressure of the subject.

Also disclosed are methods for reducing likelihood or preventing vision loss in subjects experiencing or at risk of vision loss by applying repeated remote conditioning treatments to these subjects in the amount and frequency sufficient to reduce the progression or prevent vision loss (also referred to a acquired blindness).

Further disclosed are methods for reducing inflammation in subjects at risk of or with known inflammation by applying repeatedly a therapy of remote conditioning with sufficient frequency so as to reduce the inflammation. Such inflammation may be short-term, as in after a major surgical procedure, or long-term, as in chronic inflammation of the joints for example.

Further yet disclosed are methods for improving local circulation to organs that may suffer from impaired circulation by applying a repeated regiment of remote conditioning therapy with sufficient frequency and intensity so as to improve local circulation to affected organs.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Figure 1:
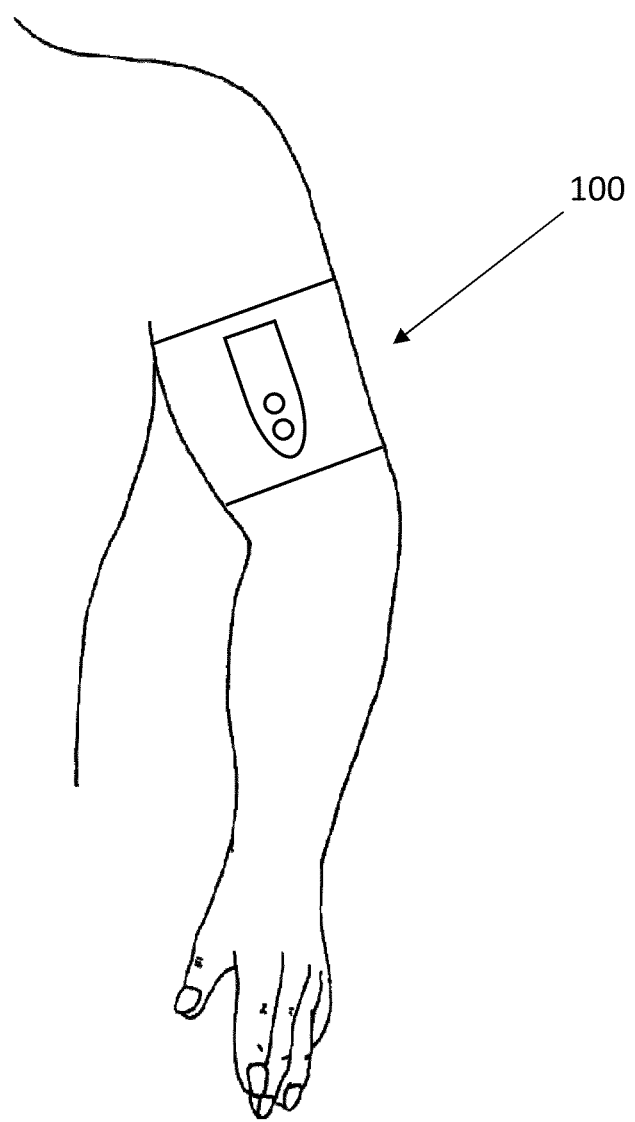
FIG. 1 is a general view of the device of the invention on a subject.
Figure 5:
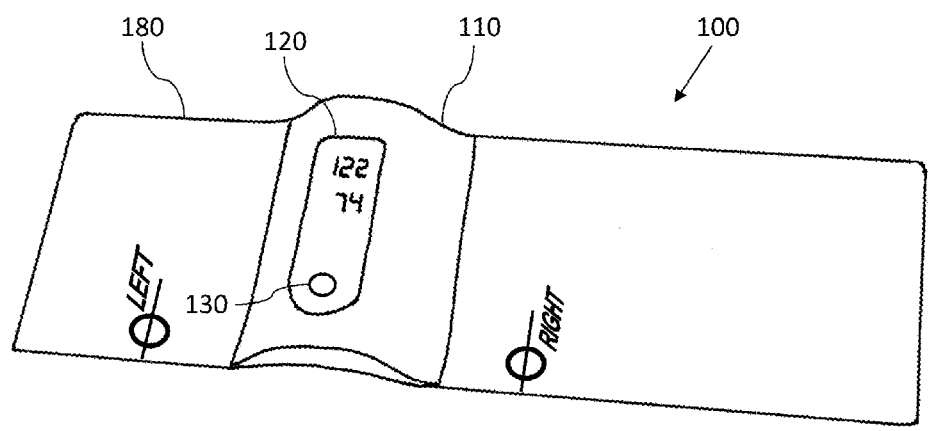
FIG. 5 shows a self-contained embodiment of the device of the present invention suitable for use in emergency circumstances.

FIG. 1 shows a general view of the device 100 on a subject with the close-up of the device 100 generally shown in FIG. 5. The device 100 includes an inflatable cuff 180 operably connected to or incorporated with a controller 110. As described in my previously filed patent applications, the cuff 180 may include a single inflatable bladder or two closely located inflatable bladders, with one bladder located distally (lower on the limb) and the other located proximally (upper on the limb and closer to the heart). The controller 110 may include a programmable processor capable of executing a program of steps to cause controlled inflation and deflation of the cuff. The controller 110 also includes a pneumatic assembly with an air pump configured for executing commands from the processor for inflating and deflating the single- or multi-bladder cuff 180.

Specific configurations of the device 100 configured for a variety of clinical applications are discussed in more details in further sections of the description.

Detecting Blood Pressure During Cessation of Blood Flow

Importantly, the controller may be configured to automatically inflate the cuff to an appropriate cuff pressure over one or more periods of cuff inflation to cause desired intervals of cessation of blood flow through the limb of the subject. The following describes the methods of cuff inflation, detecting subject's blood pressure and selecting the optimal (minimal) cuff inflation pressure.

Figure 2:
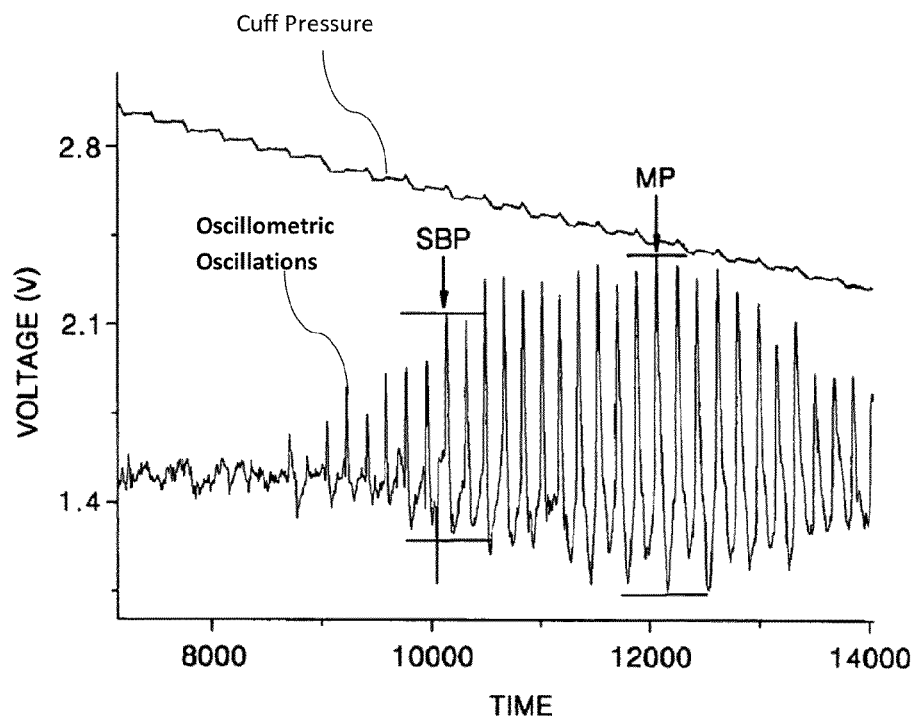
FIG. 2 is a chart depicting traditional oscillometric method of detecting blood pressure of the subject using an inflatable cuff.

FIG. 2 shows a known oscillometric method of detecting blood pressure of the subject using an inflatable cuff. The cuff is slowly inflated or deflated while oscillometric oscillations are monitored and their amplitude is detected. A point where the oscillometric amplitude has reached its maximum is declared to correspond to a cuff pressure equal to the mean arterial pressure (MP) of the subject. Systolic blood pressure is then determined by calculating the systolic amplitude of oscillations (SBP) as a certain predetermined percent of the maximum oscillations amplitude.

Importantly, even at cuff pressures above the systolic pressure, some small oscillations of oscillometric curve can still be observed. These small oscillations are caused primarily by the edge effect of the cuff—while the blood vessel under the cuff is fully occluded to cease blood flow therethrough, the upper portion of the cuff is still exposed to pulsating blood in the arterial vessels above the occluded portion of the blood vessel.

According to the present invention, there is provided a method for determining systolic blood pressure of a subject without compromising cessation of blood flow through the limb, the method comprising the following steps:

(a) providing a cuff sized to be placed about a limb of the subject, the cuff is configured (for example selected to be wide enough) to define limb occlusion pressure to be equal to or below systolic blood pressure of the subject;

(b) determining systolic blood pressure of the subject by inflating the cuff placed about the limb of the subject;

(c) inflating the cuff to a pressure slightly below (by about 1-15 mmHg), at or above the systolic blood pressure calculated in step (b) for a period of cuff inflation to cause cessation of blood flow through the limb, the period of cuff inflation lasting at least about one minute;

(d) at least once during the period of cuff inflation, decreasing cuff pressure sufficiently to determine an updated systolic blood pressure of the subject but without compromising cessation of blood flow through the limb; and (e) inflating the cuff to a pressure slightly below, at or above the updated systolic blood pressure calculated in step (d).

The methods of properly selecting the cuff to assure the limb occlusion pressure is at or below the systolic pressure of the subject are described in more detail in my cited previous patent applications.

Step (d) of the method may further include a step of decreasing cuff pressure until the amplitude of detected oscillometric oscillations increases to a predetermined threshold, indicating the cuff pressure to be equal to or below the updated systolic blood pressure but at least equal to or above a corresponding limb occlusion pressure of the subject, which is why the updated systolic blood pressure may be determined without compromising cessation of blood flow through the limb.

In embodiments, providing a wide enough cuff will assure continuous cessation of blood flow even if the cuff pressure is decreased to the updated systolic blood pressure or a few mmHg below it. At this cuff pressure, the amplitude of oscillations may be detected to be at or above the predetermined threshold but the blood flow is still stopped as the cuff pressure did not drop below the updated limb occlusion pressure.

Figure 3:
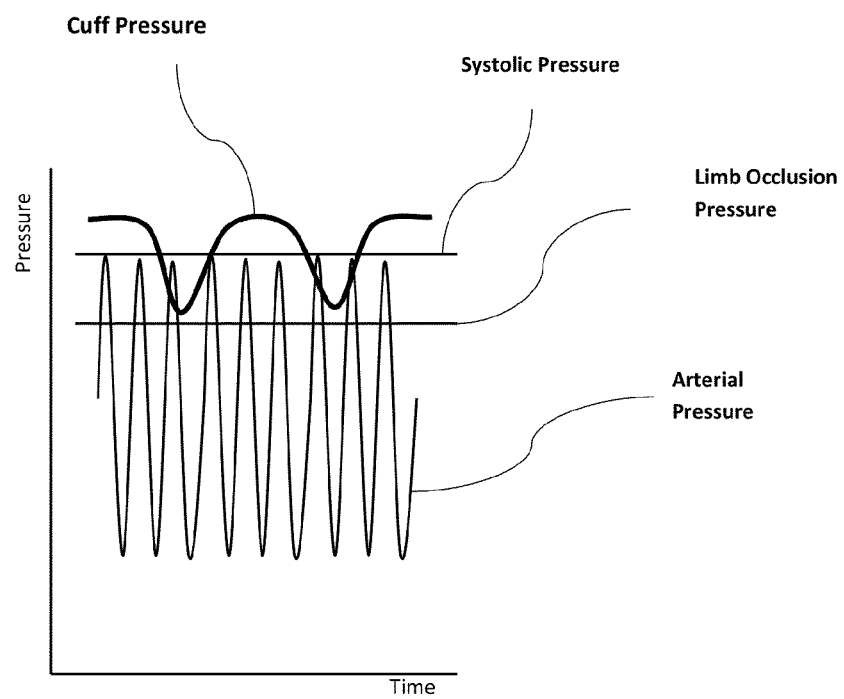
FIG. 3 is a chart showing the concept of intentional fluctuation (dithering) of the cuff pressure by the controller of the device according to the invention.

FIG. 3 shows a general approach of varying the cuff pressure according to the invention. When the cuff is selected to be sufficiently wide, the limb occlusion pressure is below the systolic blood pressure as can be seen in FIG. 3. For a standard cuff width of inflatable cuffs used for traditional blood pressure monitors, the limb occlusion pressure may be about 3 to 10 mmHg below the systolic blood pressure of the subject.

Shown in FIG. 3 is a chart of blood pressure of the subject and a pair of generally parallel lines indicating limb occlusion pressure and systolic blood pressure—in this example they are shown to be steady throughout the period of cuff inflation.

Initially, the cuff may be inflated to a pressure at or above the first determined level of systolic blood pressure. At least once (or more in some embodiments, such as on a periodic basis) after that, the cuff pressure may be decreased to a level at or below the systolic blood pressure but still at or above the limb occlusion pressure. This decrease in cuff pressure allows detecting an updated systolic blood pressure as will be described below. Once the updated systole is determined, the cuff pressure may be increased to a level slightly below, at or above the updated systolic blood pressure or at or above the updated limb occlusion pressure—by a predetermined safety margin. Once the target cuff pressure is reached, the controller may be configured to repeat the process of updating systolic blood pressure information or maintain the cuff pressure steady for a predetermined period of time. After that holding period of time has elapsed, the process of detecting updated systolic blood pressure may be repeated. In embodiments, such process of cuff pressure dithering and detecting the updated systolic blood pressure of the subject may be repeated every 5 sec; 10 sec; 20 sec; 30 sec; 45 sec; 1 min; 3 min; 5 min; 10 min; 30 min; 60 min or at any frequency in-between.

The desired frequency of updating the systolic blood pressure information may depend on the clinical situation and the health of the subject. In embodiments, the frequency of updates may be fixed and such updates may be programmed to be performed on a scheduled basis. In other embodiments, adaptive schedule of blood pressure updates may be implemented: in one example, a series of previous blood pressure updates may be analyzed for consistency and stability of systolic blood pressure values. If systolic blood pressure is stable, the frequency of updates may be reduced. If strong blood pressure fluctuations are encountered, the frequency of updates may be adaptively increased. For battery-operated devices, consideration must be given to power consumption needed to operate the air pump and other components of the device for determination of updated blood pressure—frequent updates may cause undesirable increase in power consumption and shorten available battery life.

Steps (c) and (e) may further be conducted by inflating the cuff to a pressure exceeding either the updated systolic blood pressure or, optionally, the calculated limb occlusion pressure by a predetermined safety margin, for example 1 mmHg; 5 mmHg; 10 mmHg; 15 mmHg; 20 mmHg; 30 mmHg; 50 mmHg; 70 mmHg or any value in-between.

Figure 4:
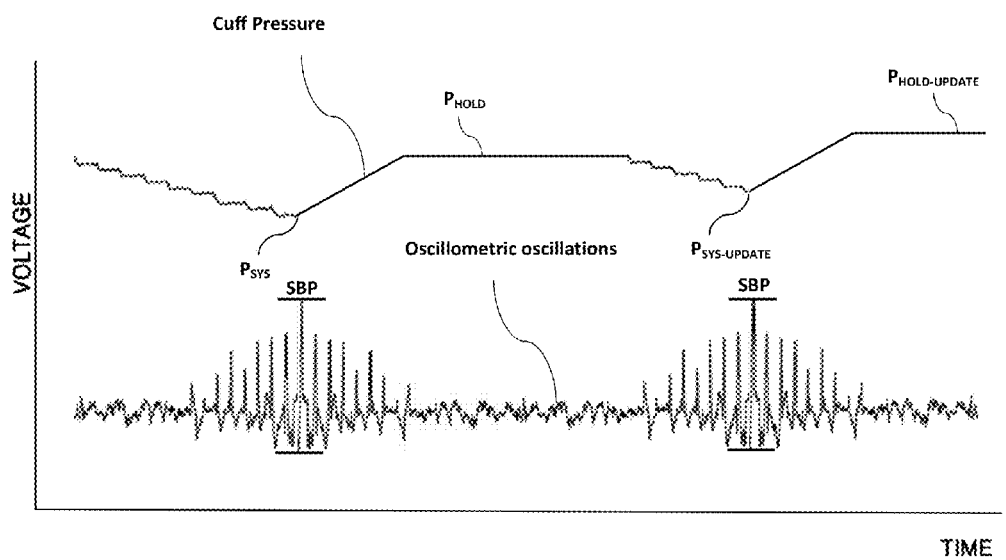
FIG. 4 is a chart showing the details of oscillometric oscillations when cuff pressure is fluctuated as shown in FIG. 3.

FIG. 4 further expands on the novel methods of detecting systolic blood pressure without compromising cessation of blood flow through the limb. Shown in FIG. 4 are two charts: cuff pressure chart is seen on the top of FIG. 4 and corresponding oscillometric oscillations chart is seen on the bottom. Cuff pressure signal may be measured by using an appropriate pressure sensor as is known in the art and then the oscillations chart may be extracted therefrom.

As described above, the initial cuff inflation may be conducted to a predetermined target pressure presumed to be above the systolic pressure of the subject, such as 160 mmHg or 200 mmHg for example. The cuff pressure may then be gradually decreased—continuously or in small steps as shown in FIG. 4. At some point during the initial decreasing of cuff pressure, the amplitude of oscillometric oscillations will start to increase and then it will reach the predetermined threshold indicating that the cuff pressure at this moment has reached the systolic blood pressure level (SBP). Once the amplitude of oscillations has reached that level and the systolic pressure $P_{SYS}$ is determined, the cuff pressure may no longer be allowed to decrease any further. Rather, the controller may activate the pneumatic assembly to bring the cuff pressure higher to a holding pressure $P_{HOLD}$ to be equal or above either the detected systolic pressure or the calculated limb occlusion pressure by a predetermined safety margin, whereby the cuff is inflated to an inflated state. When the cuff pressure may thus be increased, the amplitude of oscillometric oscillations will decrease to noise levels as seen in FIG. 4.

The controller may further be programmed to start a new procedure of detecting updated systolic blood pressure—immediately after completion of the previous procedure or after a predetermined time interval has elapsed. During this process, the cuff pressure may again be gradually decreased while the amplitude of oscillometric oscillations may be monitored. Once this amplitude reaches the predetermined threshold, further decrease in cuff pressure may be halted and the updated systolic blood pressure $P_{SYS-UPDATE}$ may be determined. After that, the controller may be programmed to increase the cuff pressure by the predetermined safety margin to the new value of holding pressure $P_{HOLD-UPDATE}$, which in this example is shown to be higher than the previous value— indicating that the systolic blood pressure had increased from the previous value. As the cuff pressure is increased once again after this determination is made, the amplitude of oscillometric oscillations will decrease once more as shown on the right side of FIG. 4. Periodic dithering of cuff pressure (increasing and decreasing as described above) allows frequent detection of the updated information about the systolic blood pressure without compromising cessation of blood flow to the limb because cuff pressure is not decreased to levels below the most current level of limb occlusion pressure.

Oscillometric oscillations may be continuously or intermittently monitored generally throughout the period of cuff inflation, for example during the holding period when the cuff pressure is held at a steady level. If an increase in the amplitude is detected, that may indicate that the systolic blood pressure of the subject is rising. If the amplitude of oscillometric oscillations reaches the predetermined threshold, the controller may be programmed to update the systolic blood pressure value and inflate the cuff to a new holding pressure exceeding the updated systolic blood pressure by the predetermined safety margin.

The predetermined threshold value for the amplitude of oscillometric oscillations indicating the new level of systolic blood pressure may be a fixed value derived from a plurality of subjects. In other embodiments, it may be derived from the most recent recording of the full oscillometric envelope for this very subject conducted during the full inflation or full deflation of the cuff. In this latter case, the maximum value of the oscillometric amplitude may be first measured and designated as indicating a mean arterial blood pressure. After that, a certain portion of that value (such as about 55%) may be determined and used to define the SBP threshold value for the subject of the therapy.

In embodiments, other methods of detecting a meaningful increase in the amplitude of oscillometric oscillations indicating the cuff pressure reaching systolic blood pressure may also be used. One example of such methods is based on analyzing the rate of amplitude increase from one heart beat to another.

The above described methods of inflating the cuff to cause cessation of blood flow through the limb while tracking fluctuations in systolic blood pressure allow the device of the present invention to occlude the limb at the minimal cuff pressure. This can be achieved by programming the controller to frequently update systolic blood pressure information (such as every 10-30 sec) while selecting a low safety margin (5-20 mmHg) for inflating the cuff above the detected levels of systolic blood pressure (or in other embodiments, the calculated limb occlusion pressure). Minimal cuff pressure is beneficial for reducing tissue compression, subject's pain during the period of cuff inflation and minimizing the risk of nerve and tissue damage, which may be otherwise caused by prolonged occlusion of the limb at higher cuff pressures.

Various specific device configurations are described below.
Smart Tourniquet

Tourniquets have been used for thousands of years to stop bleeding of the extremity as a result of various wounds, cuts, accidents etc. Various types of improvised or manufactured self-contained tourniquets are well known in the art. Loss of blood is a major cause of death in military combat and emergency situations, in which the injured person may be alone or medical assistance may not be immediately available. The use of a tourniquet to stop blood loss from an injured arm or leg is a well-known technique for preventing death in these situations. Once the primary objective of preventing death due to blood loss is achieved, it is desirable to prevent further injury to the limb due to excessive pressure and time of tourniquet application. To minimize mechanical injury to the tissues under the tourniquet, the pressure applied by the tourniquet should be at or only slightly higher than that required to stop blood flow. In addition, the tourniquet pressure should be applied evenly and uniformly around the limb beneath the tourniquet, without localized regions of very high or very low pressures. To help prevent gangrene and other complications related to the lack of arterial blood flow into the portion of the limb distal to the tourniquet, it is widely accepted that the tourniquet pressure should be at least partially released for a period of 5-15 minutes and then reapplied after each 2 to 3 hour period of stoppage of arterial blood flow.

Mechanical tourniquets such as various strap and ratchet-type tensioning devices while capable of applying compression to the limb, are limited in the proper application of limb compression. Controversy about the proper use of such devices is continuously debated in the literature as there is no simple way to apply the right degree of limb compression— ideal compression should not be too loose to risk internal or external bleeding; and not too tight so as to cause nerve and tissue damage. Applying a tensioning tourniquet properly is not an easy task even for an experienced medical professional, let alone a medically untrained and wounded soldier on the battlefield.

The device of the present invention may be advantageously configured to operate as a smart tourniquet, which can be activated with a push of a single START button 130. This device is generally shown in FIG. 5 and broadly described above. It includes a cuff 180 and a battery-operated controller 110 incorporated therein or attached thereto. For the purposes of serving as a smart tourniquet, the controller 110 (once activated after the device 100 is placed over the limb) may be configured to determine the minimal limb occlusion pressure and inflate the cuff to a pressure exceeding the limb occlusion pressure by a predetermined safety margin—using the methods described in greater detail above and shown in FIG. 3 and FIG. 4. The duration of cuff inflation period may be determined to not exceed 2-3 hours after which the device may be programmed to automatically release cuff pressure (partially or entirely) for a short period of time—generally 5-20 min long—and then re-inflate the cuff to continue the tourniquet function. The display may be configured to communicate to the user the elapsed duration of cuff inflation time, last measured systolic blood pressure and other pertinent information.

The controller may be configured to periodically update the systolic blood pressure information and adjust the cuff pressure accordingly. The controller may further be configured to detect if the systolic blood pressure has dropped below a predefined safe limit and activate an optional alarm, such as audio-, visual- or an alarm which may be remotely transmitted via radio or another wireless transmission. Such remote transmission and wireless communication with a central monitoring station may include periodic updates on the subject's blood pressure or a heart rate, which may further facilitate appropriate triage of patients depending on their hemodynamic status. A GPS location beacon may also be incorporated into the smart tourniquet of the invention, which can be used to find the injured or wounded subject.

Due to its automatic nature and sophisticated methods of monitoring hemodynamics, practically no skills are required from the user to properly use the tourniquet of the invention. In many cases, it can even be self-applied. Small size and weight of the device make it advantageous for use for a variety of applications, such as in a military setting, extreme sports, high altitude climbing, etc. In addition to being simple in use, the device of the invention may be configured to advantageously select the minimal initial cuff inflation pressure, adjust the cuff pressure during the period of cuff inflation if necessary to track the blood pressure of the subject, and automatically restore perfusion for short intervals of time to flush out metabolites from the injured tissue.

While in some embodiments, the cuff may comprise a single inflatable bladder, in other embodiments the cuff may comprise a proximal inflatable bladder and a distal inflatable bladder as described in my previously filed patent applications. For dual-bladder tourniquets, the distal bladder may be continuously inflated to a fixed or adjusted pressure at or above either the limb occlusion pressure or the systolic blood pressure. At the same time, the proximal bladder may be inflated and dithered about the systolic blood pressure as described above for FIG. 4 so as to monitor fluctuating blood pressure of the subject. Cuff pressure in both bladders may be adjusted from time to time if a meaningful change in systolic blood pressure of the subject is detected.

Another method of operating the dual bladder tourniquet is to use the distal (lower) bladder for the purposes of occluding blood flow while the proximal (upper) bladder may be fully inflated and deflated to determine the values of systolic, mean, and diastolic blood pressures. Following cuff inflation, the deflation of the cuff may be conducted starting at levels at or above the limb occlusion pressure and extended down to cuff pressures below the limb occlusion pressure and even through the mean arterial pressure and further down to diastolic pressure. Blood flow to the limb will still be stopped by the inflated distal bladder. This configuration allows periodic updates to the entire blood pressure information of the subject, not just the systolic blood pressure.

In embodiments, the controller may be further programmed to vary the cuff pressure and monitor the resulting increase in distal blood flow in order to determine whether the use of tourniquet is even appropriate in the first place or should be continued. It is known that tourniquets may be applied mistakenly when the level of bleeding is not that high as to cause severe blood loss. In these cases, excessive and prolonged tissue compression may cause more harm than good. While the smart tourniquet of the invention will diminish the risk of severe tissue compression by inflating the cuff to a minimum effective cuff pressure using techniques described above, further methods of automatically detecting the severity of the wound may be implemented to allow selecting of the most appropriate course of automatic operation.

Two types of limb wounds may be defined: those with or without a severe cut in a major blood vessel. Severe damage to a major blood vessel may be life-threatening. To distinguish between the two types of wounds, the controller may be programmed at least once during the period of cuff inflation to take the following steps:

(a) inflate the proximal and distal bladders to a pressure at or above the limb occlusion pressure to prevent any blood loss;

(b) decrease the proximal bladder pressure to measure at least the systolic blood pressure, mean arterial pressure or the diastolic blood pressure of the subject—with no flow under the tourniquet;

(c) partially or fully decrease the distal bladder pressure below the limb occlusion pressure to cause at least partial or full restoration of blood flow under the tourniquet for a short period of time (between 2 and 30 sec), spanning at least one or several consecutive heart beats of the subject;

(d) re-inflate the proximal bladder while recording the oscillometric envelope and detecting at least the systolic blood pressure, mean arterial pressure, or the diastolic blood pressure of the subject while blood flow to the limb is at least partially or fully restored; and (e) compare the measurements of respective blood pressures or the degree of their oscillations obtained in steps (b) and (d)—a difference above a predetermined threshold would indicate lack of back pressure and the presence of severe damage to the major blood vessel downstream from the tourniquet.

Alternatively, the controller may be programmed to first inflate both inflatable bladders to a pressure at or above the limb occlusion pressure and then decrease the proximal bladder pressure to below the limb occlusion pressure while keeping it above the diastolic blood pressure of the subject, for example to the mean arterial pressure where the amplitude of oscillometric oscillations is the highest. At this bladder pressure, the portion of the major artery located under the proximal bladder will be partially collapsed. The controller may be then programmed to reduce the distal bladder pressure below the limb occlusion pressure so as to partially or fully release compression of the limb downstream causing blood flow to be at least partially or fully restored. Observations of the amplitude of oscillations under the proximal bladder may reveal the degree of vessel damage—if the amplitude is reduced below a predetermined threshold, there is little or no back pressure downstream from the tourniquet indicating that the wound is severe. On the other hand, If the amplitude did not change appreciably, the wound may be minor and the cuff may be safely removed.

Three-in-One Smart Tourniquet

A further advantageous configuration of the device may include the ability of a single device to operate independently in one, two, or all three operating modes: as an emergency tourniquet; as a blood pressure monitor; or as a remote conditioning delivery tool. Appropriate user interface may be provided to allow the user to select the desired one or more modes of operation.

Small size and weight of such device makes it advantageous for military use as well as for applications in which the weight and size of emergency medical equipment is limited.

While in a tourniquet mode, the device of the invention may operate by inflating the cuff to a manually-set or predetermined pressure or by automatic operation as described above.

In the blood pressure monitoring mode, the device may perform traditional inflation and deflation of the cuff and display the results of obtained blood pressure to the user. If the blood pressure monitoring feature is desired to be active while in a tourniquet or remote conditioning mode, the device may be configured to provide at least systolic blood pressure value. It embodiments, it may also provide estimated diastolic blood pressure and estimated mean arterial pressure while the limb is still occluded.

In a remote conditioning mode, the device of the invention may operate automatically by periodically inflating the cuff to cause cessation of blood flow to the limb according to a remote conditioning treatment protocol as described above.

In addition to independent operation in one or two modes of operation at the same time as described, the controller may be programmed to provide a predetermined sequence of operating modes, for example upon completion, the remote conditioning mode or the tourniquet mode may be automatically followed by a blood pressure monitoring mode when blood pressure is determined on a manually set or preprogrammed schedule, such as every 5 min or every 10 min.

Patient Monitor with a Remote Conditioning Mode of Operation for Hospital Use

The benefits of remote conditioning therapy are attractive in a number of clinical circumstances when prolonged interruption of blood flow is a scheduled event—such as for example during various surgeries including coronary artery bypass surgery, percutaneous coronary intervention, abdominal aortic aneurysm surgery, major kidney or liver surgery and alike. As opposed to emergency circumstances when time is of the essence and the subject may be frequently transferred from one department to the other, whereby making a disposable device of the invention convenient, such scheduled events are highly predictable. In these circumstances, the subject generally remains in one place and can receive the therapy of remote conditioning on a scheduled basis with a reusable configuration of the device.

Figure 6:
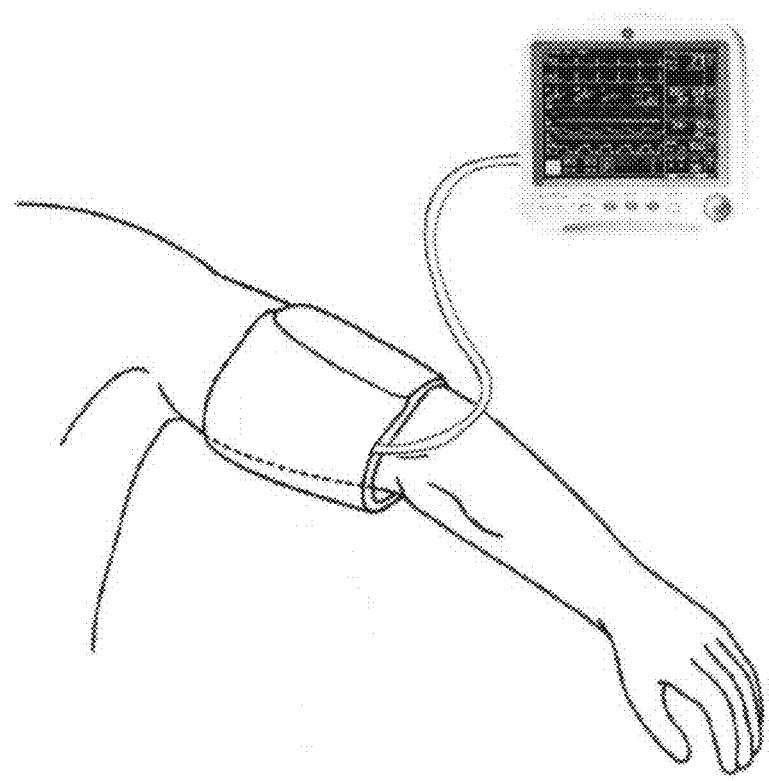
FIG. 6 shows a general outline of the device configured for use in conjunctions with a hospital patient monitor.

This reusable configuration of the device is shown generally in FIG. 6. A hospital-grade patient monitor, which typically operates to measure subject's blood pressure using an inflatable cuff, may be configured to include a remote conditioning mode of operation. Same or similar hardware may be used for such device as with traditional hospital patient monitors and inflatable blood pressure measuring cuffs. Appropriate user interface may be added to allow the user to activate the remote conditioning mode and operate the device to inflate and deflate the cuff for delivery of remote conditioning as described above. While blood pressure may be monitored using traditional oscillometric methods either before or after the delivery of remote conditioning, using the novel cuff inflation methods described above for FIGS. 3 and 4 allows continuing hemodynamic monitoring throughout the 40-min period of remote conditioning.

Another advantage of using the methods of the invention is that the delivery of remote conditioning therapy will proceed at the minimum cuff pressure, thereby reducing the discomfort of the subject.

A further advantage of using the methods of the invention in this product configuration is that a single patient monitor and a single cuff may be used for both hemodynamic monitoring and delivery of remote conditioning therapy, obviating the need to add a second monitor and a second cuff on the other arm of the subject to monitor blood pressure and other vital signs during the period of delivery of remote conditioning.

Blood Pressure Monitor with a Remote Conditioning Mode of Operation for Home or Public Place Use Because of its demonstrated clinical benefits, simplicity and excellent safety profile, remote conditioning may be applicable in settings outside the hospital, such as for home use or for use in public places.

Figure 7:
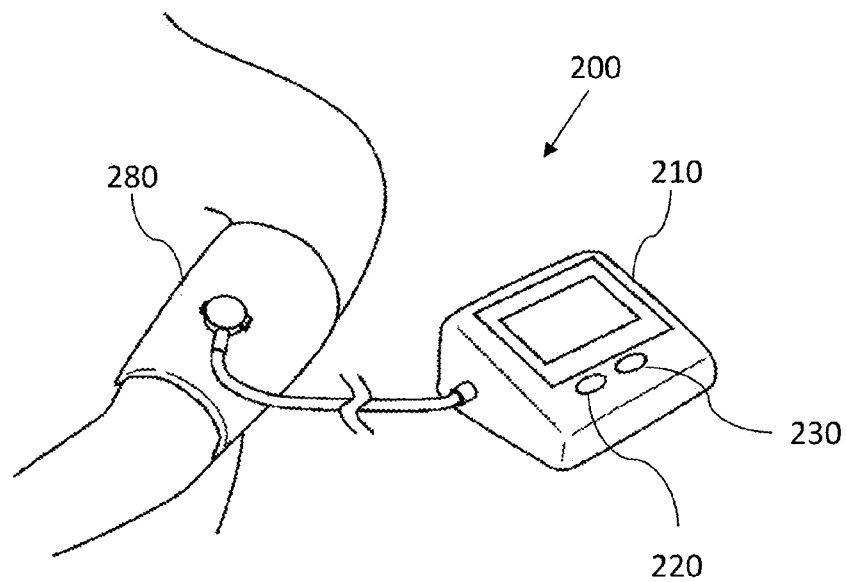
FIG. 7 shows a general outline of the device configured for use at home.

A home-based blood pressure monitor may be configured to provide remote conditioning therapy to subjects that may benefit from it. One example of such device 200 is generally shown in FIG. 7 and includes a cuff 280 connected to a controller 210. As opposed to a traditional blood pressure monitor, the controller 210 may be equipped with a user interface allowing for mode selection, for example a button 220 for activation of a traditional procedure to measure blood pressure and another button 230 for activation of remote conditioning therapy.

Another configuration of the device includes incorporating a remote conditioning mode with publically available stations for blood pressure monitoring. Such stations are commonly available in pharmacies and malls where a lay person may come in and check his or her blood pressure. One example of such device is described in the U.S. Pat. No. 4,998,534 incorporated herein by reference.

As described in more detail below, many subjects may benefit from repeated application of remote conditioning. As they may not have an appropriate device at home or may be reluctant to self-apply the therapy using a manually-inflated blood pressure cuff, publically available blood pressure monitoring stations may be equipped with a remote conditioning mode of operation to provide the benefits of the remote conditioning therapy to the public. Such devices may be configured to provide remote conditioning treatments free of charge as a public service or on a fee-for-service arrangement. Advantageously, even if the therapy is delivered free of charge, the establishment providing such equipment may still benefit commercially by having a repeated flow of customers who come to the establishment on a periodic basis. To further increase the economic benefit, an audio or visual messaging may be provided to the subject during the 40-min procedure of remote conditioning. Such messaging may include entertainment, health-oriented information or commercial advertisement.

Various types of patients may benefit from repeated remote conditioning, including patients with known increased risk of a heart attack or stroke, elderly patients, and diabetics.

Another category of such patients are those who underwent a recent major surgery. Remote conditioning may release anti-inflammatory substances and repeated application of the therapy may help to speed up recovery and various postoperative healing processes.

Anti-inflammatory action of the therapy may be also used to improve a variety of clinical conditions involving inflammation—both as a single application as well as a result of its chronic administration over weeks, months and even years. Examples of such inflammation conditions may include back pain, arthritis, joint pain, neuralgia, other types of nerve impingement, headache, migraine multiple sclerosis, etc.

New aspects of this therapy are discovered every day and may provide for other yet unknown therapies and treatments. In fact, the therapy may have non-clinical benefits—it has been reported to improve human physical performance and resilience, improve survival in harsh environmental conditions such as high altitude, extreme heat, etc.

Remote conditioning is further believed to provide neurologic benefits and preserve neurons in the brain and in the optical nerve tissues, which otherwise may get damaged during traumatic brain injuries, strokes or as a result of debilitating diseases such as diabetes or glaucoma.

According to the invention, repeated application of remote conditioning may be utilized to prevent or at least postpone the onset of vision loss or acquired blindness as a result of such debilitating conditions as diabetic retinopathy, glaucoma or age-related macular degeneration. These conditions involve damage to the optical nerve tissues—mostly as a result of ischemia via apoptosis caused by damage to the mitochondria.

Ischemic conditioning is the most potent known method of protecting mitochondria from ischemic damage. According to the invention, periodic application of the therapy may provide a clinical benefit of reducing vision loss or at least in slowing down its progression. The therapy may be applied with a frequency of twice-a-day, once-a-day, twice-per-week, once-per-week, once every two weeks or another desired frequency in-between or with the frequency shown to be sufficient for this purpose. In the US alone, there are about 5 million patients diagnosed with diabetic retinopathy and about another 25 million diabetics who are at risk of developing this condition. In addition, there are about 3 million patients with diagnosed glaucoma and another 2 million with diagnosed age-related macular degeneration. Together, these patients constitute a market opportunity for tens of millions of home-based devices in US alone.

According to the invention, remote conditioning is further believed to improve over a long-term blood flow to organs with impaired circulation. Arterial stenosis or other types of arterial narrowing may be improved by repeated application of remote conditioning especially if they are caused by or at least contributed to by endothelial dysfunction. The methods of the invention comprise applying repeated remote conditioning treatments to subjects with impaired local circulation (optionally supplemented with appropriate medication) with sufficient frequency and intensity (number of cycles and duration or limb occlusion) in order to improve local organ circulation.

The advantage of using adaptive methods of inflating the cuff as described above for all of these treatment methods (as compared with other methods of cuff inflation for remote conditioning using fixed inflation pressure) is that adaptive cuff inflation allows minimizing cuff inflation pressure and therefore decreasing subject's pain. This is especially beneficial if the therapy is applied frequently, over a long period of time and to vulnerable pain-sensitive patient populations such as the elderly.

Orthopedic Surgery Tourniquet with Blood Pressure Monitoring Mode of Operation

Yet another configuration of the device of the invention is that tailored for use during orthopedic surgery or other surgery of the extremity involving a tourniquet placed on the leg or an arm and inflated for prolonged periods of time to assure bloodless field of operation.

Known are devices configured for determination of limb occlusion pressure using a blood flow sensor placed on a toe of the subject, such as a plethysmographic or pulse oximetry sensor. One example of such device is Automatic Tourniquet System ATS 3000 manufactured by Zimmer Inc. (Warsaw, Ind.). The controller of this device is configured to inflate the cuff to a point when blood flow is no longer detected by the sensor downstream from the cuff—this allows the controller to detect the limb occlusion pressure.

This design is limited in that limb occlusion pressure can be determined only once—before inflating the tourniquet and starting the surgery. Repeated determination of the limb occlusion pressure using a downstream sensor is not possible—a deep enough decrease of the cuff pressure necessary to detect onset of blood flow by the downstream sensor will cause bleeding at the surgical site. Because blood pressure may vary during surgery, such initial determination of limb occlusion pressure is used only in an advisory capacity prompting the user to set the cuff inflation manually—usually with a high safety margin for a target cuff pressure for the tourniquet, so as to avoid possible bleeding at the surgical site at a later time, when the blood pressure may increase.

The present invention addresses this limitation by providing a novel ability to monitor systolic blood pressure not downstream but upstream of the cuff, using cuff inflation methods described above. Such monitoring may be conducted once or multiple times throughout surgery and the cuff pressure may be adjusted accordingly if the systolic blood pressure is seen as drifting up or down. This design has several advantages over the previous design:

proper initial inflation and periodic adjustment in cuff pressure may be done automatically, the user only has to initiate the operation of the device by pressing a single START button—this simplifies significantly the use of the device;

determination of the systolic blood pressure may be done automatically both before and during surgery;

low safety margin may be selected leading to lower cuff inflation pressure;

cuff pressure may be automatically adjusted throughout surgery—without further user involvement;

current blood pressure may be displayed for medical practitioner to observe; and finally no additional sensor is needed to be positioned on the toe of the subject.

Figure 8:
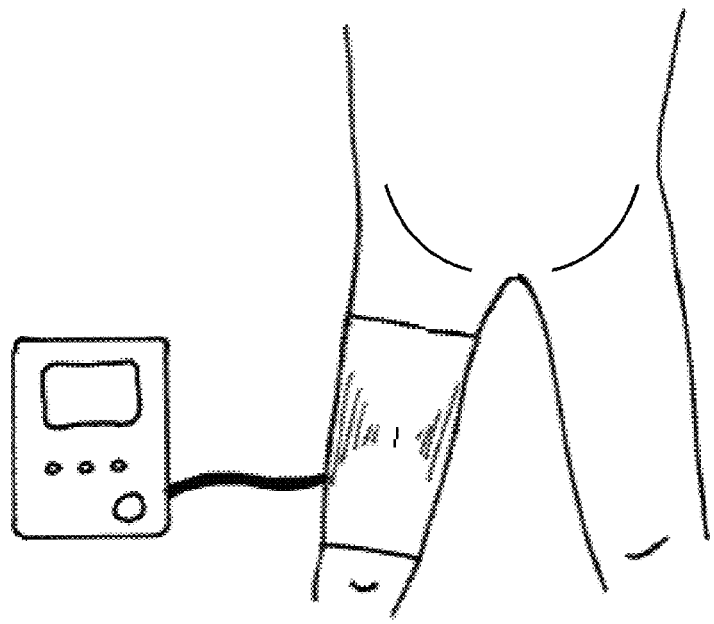
FIG. 8 shows a general configuration of the device configured for use during orthopedic surgery.

In embodiments of the invention, there is provided a device including a controller operably connected to a cuff sized to be positioned about the upper leg of the subject—see FIG. 8. The controller may be configured to inflate the cuff in a tourniquet mode in a manner similar to that described above for the tourniquet designed to control blood loss. The controller may have an automatic mode of operation, in which once activated, the controller will first determine the initial limb occlusion pressure and then inflate the cuff to a pressure exceeding that minimum level by a predetermined safety margin. At least once or on a periodic basis throughout surgery, the controller may be programmed to automatically decrease the cuff pressure to the point when the amplitude of oscillometric oscillations has reached a predetermined threshold, at which time the updated systolic blood pressure is determined and the cuff is inflated to an adjusted cuff pressure target as described in more detail above.

The controller may be programmed to periodically check the current level of systolic blood pressure of the subject and automatically adjust the cuff pressure accordingly throughout the period of cuff inflation. Such operation assures minimum tissue compression while tracking blood pressure over the period of surgery.

In other embodiments, the cuff may have a dual-bladder design and the controller may have two ports for operating the bladders separately. In one example of a tourniquet mode of operation, the distal bladder may be inflated to cause cessation of blood flow to the limb while the proximal bladder may be operated to periodically check blood pressure of the patient. Once a shift in blood pressure is detected, cuff pressures in both bladders may be accordingly adjusted.

Orthopedic Surgery Tourniquet with Remote Conditioning Mode of Operation

Total knee arthroplasty is one of the most painful procedures postoperatively, and pain management can be a challenge. Excessive acute pain after total knee arthroplasty can complicate early postoperative rehabilitation if uncontrolled. This pain is commonly managed with medications, which can be associated with an increased risk of addiction and a variety of side effects, including sedation, confusion, and falls. These side effects are particularly common among the elderly, who undergo the majority of these procedures. Adding an adjunct non-pharmacologic therapy for improved wound healing and pain management that can decrease the use of medication during the early post-operative period following total knee arthroplasty would be beneficial to patient recovery.

Ischemia-reperfusion injury is a known consequence of arresting blood flow for a prolonged period of time. Surgical tourniquet placed on the upper leg to create a bloodless field for total knee arthroscopy procedure is known to cause such injury when it is removed. Ischemia-reperfusion injury may increase the surgical trauma and lead to increased postoperative pain. Ischemic conditioning is a known therapy to generally reduce ischemia-reperfusion injury. According to the invention, it may also be effective in reducing post-operative pain and improving overall post-op recovery in knee arthroscopy procedures.

Figure 9:
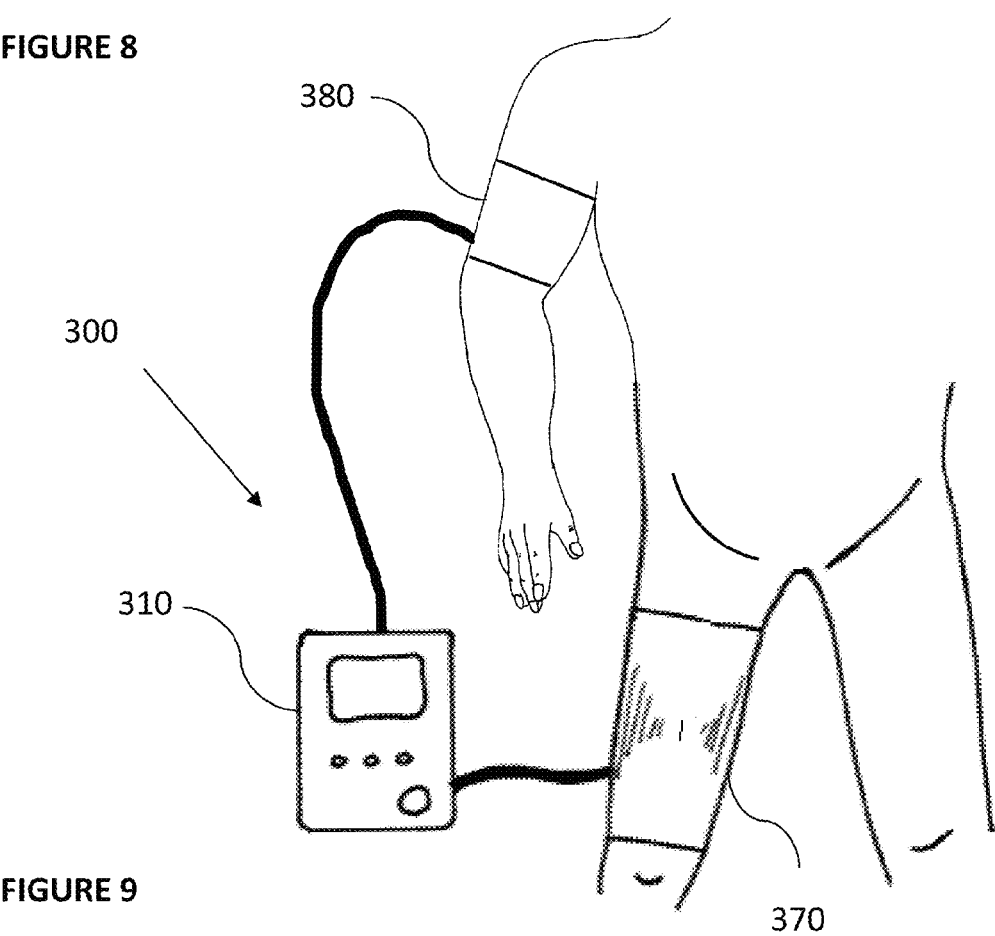
FIG. 9 shows a controller connected to two cuffs placed about two limbs of the subject, one cuff is operated in a remote conditioning mode and another cuff operated in a tourniquet mode.

The device 300 of the invention is generally shown in FIG. 9. It comprises a controller 310 connected to at least a first cuff 370 positioned about a first extremity such as an upper thigh. The first cuff 370 may have in turn a single bladder or a dual bladder design as known in the art of inflatable orthopedic tourniquets.

The controller 310 may also be configured to be attached to a second cuff 380 positioned about a second extremity such as an upper arm. In embodiments, the controller 310 may have a single cuff attachment port adapted to be connected to either the cuff 370 or the cuff 380 at different times during the surgery. In other embodiments (as seen in FIG. 9), the controller may be equipped with two cuff attachment ports and configured to inflate and deflate the cuffs 370 and 380 independently, including on an overlapping schedule. In yet other embodiments, when the cuff 370 has two inflatable bladders, the controller 310 may have three cuff attachment ports: two for operating a dual-bladder cuff 370 and one for operating a single bladder cuff 380.

In embodiments with the controller 310 attached to a single cuff 370, the controller 310 may be configured to operate first in a remote conditioning mode and then in a tourniquet mode as described above. In other embodiments, the controller 310 may be configured to first operate in a tourniquet mode and then in remote conditioning mode to provide the subject with the benefit of remote post-conditioning. Note that while in a remote conditioning mode, the cuff 370 may be placed either on the limb to be operated on (such as the leg subject to knee replacement) or on an alternative limb (such as an upper arm). Obviously, after the remote conditioning is complete, the cuff 370 has to be moved to the place of surgery.

In other embodiments, when the controller 310 is attached to both cuffs 370 and 380, remote conditioning mode may be activated for the cuff 380 while the cuff 370 may be operated in a tourniquet mode. Both modes may be activated independently, for example remote conditioning with cuff 380 may be initiated prior to the inflation of the cuff 370 in a tourniquet mode. In other embodiments, the dual operation of the cuffs may be conducted such that remote conditioning may be timed to conclude close to the conclusion of knee surgery and deflation of the cuff 370, thereby maximizing the benefit of remote conditioning in reducing ischemia-reperfusion injury of the leg tissues.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for adaptive limb occlusion of a subject, the method comprising the steps of:
   (a) providing a cuff sized to be placed about a limb of the subject, said cuff is configured to define a limb occlusion pressure to be equal to or below a systolic blood pressure of the subject;
   (b) determining the systolic blood pressure of the subject by inflating the cuff placed about the same limb of the subject;
   (c) inflating the cuff to a pressure sufficient to cause cessation of blood flow through the same limb, said pressure being below, at or above the systolic blood pressure calculated in step (b) for a period of cuff inflation, said period of cuff inflation lasting at least about one minute;
   (d) at least once during the period of cuff inflation, decreasing entire cuff pressure until detecting an increase in oscillometric oscillations indicating the cuff pressure to be above, equal to, and capable of being below an updated systolic blood pressure while at least equal to or being above the corresponding limb occlusion pressure of the subject, whereby said entire cuff pressure is decreased sufficiently to determine the updated systolic blood pressure of the subject but without compromising cessation of blood flow through the same limb; and
   (e) inflating the cuff to a pressure below, at or above the updated systolic blood pressure calculated in step (d), said pressure being sufficient to continue causing cessation of blood flow through the same limb.

2. The method as in claim 1, wherein the cuff is inflated in steps (c) and (e) to the pressure at or above the limb occlusion pressure.

3. The method as in claim 1, wherein said step (d) further including a step of decreasing cuff pressure until an amplitude of detected oscillometric oscillations increases to a predetermined threshold indicating the cuff pressure to be equal to or below the updated systolic blood pressure but at least equal to or above the corresponding limb occlusion pressure of the subject, whereby the updated systolic blood pressure is determined without compromising cessation of blood flow through the limb.

4. The method as in claim 1, wherein said steps (d) and (e) are repeated on a scheduled basis throughout the period of cuff inflation.

5. The method as in claim 1, wherein said steps (c) and (e) are conducted by inflating the cuff to a pressure exceeding the systolic blood pressure by a predetermined safety margin.

6. The method as in claim 1, wherein step (a) further comprising providing a controller operably connected to said cuff, said controller is configured to automatically perform said steps (b) through (e).

7. A method for adaptive limb occlusion of a subject, the method comprises the steps of:
   (a) providing a cuff placed about the limb of the subject, the cuff configured to define a limb occlusion pressure to be equal to or below a systolic blood pressure of the subject;
   (b) inflating the cuff to a pressure at or above the limb occlusion pressure of the subject for a period of cuff inflation lasting at least one minute;
   (c) continuously or intermittently monitoring cuff pressure for an indication that the entire cuff pressure is at or below systolic blood pressure of the subject; and (d) upon the indication that the entire cuff pressure is at or below the systolic blood pressure of the subject and the cuff pressure is at or above the limb occlusion pressure of the subject, inflating the cuff to a pressure exceeding the limb occlusion pressure by a predetermined safety margin, whereby maintaining cessation of blood flow to the same limb throughout the period of cuff inflation.

8. The method as in claim 7, wherein said step (c) further including deflating said cuff at least once during said period of cuff inflation until reaching a predetermined increase in oscillometric oscillations within said cuff.

9. The method as in claim 8, wherein in step (c) said predetermined increase in oscillometric oscillations is determined analyzing an amplitude of said oscillometric oscillations.

10. The method as in claim 9, wherein in step (c) said predetermined increase in oscillometric oscillations is determined by detecting said amplitude reaching a predetermined amplitude threshold.

11. The method as in claim 9, wherein in step (c) said predetermined increase in oscillometric oscillations is determined by analyzing a rate of increase of said amplitude.

* * * * *